(12) United States Patent
Marshall et al.

(10) Patent No.: US 8,221,741 B2
(45) Date of Patent: Jul. 17, 2012

(54) METHODS FOR MODULATING INFLAMMATORY AND/OR IMMUNE RESPONSES

(76) Inventors: Vivienne S. Marshall, Glenshaw, PA (US); Richard A. Banas, Turtle Creek, PA (US); Catherine J. Trumpower, Pittsburgh, PA (US)

( * ) Notice: Subject to any disclaimer, the term of this patent is extended or adjusted under 35 U.S.C. 154(b) by 68 days.

(21) Appl. No.: 12/448,903

(22) PCT Filed: Jan. 11, 2008

(86) PCT No.: PCT/US2008/000396
§ 371 (c)(1),
(2), (4) Date: Jul. 13, 2009

(87) PCT Pub. No.: WO2008/088738
PCT Pub. Date: Jul. 24, 2008

(65) Prior Publication Data
US 2010/0068180 A1    Mar. 18, 2010

Related U.S. Application Data

(60) Provisional application No. 60/880,745, filed on Jan. 17, 2007, provisional application No. 60/902,440, filed on Feb. 21, 2007, provisional application No. 60/997,604, filed on Oct. 4, 2007.

(51) Int. Cl.
*A61K 39/00* (2006.01)
*A61K 35/12* (2006.01)
*A61K 38/21* (2006.01)

(52) U.S. Cl. ............... 424/93.21; 424/93.7; 424/184.1; 424/141.1; 424/173.1

(58) Field of Classification Search .................. None
See application file for complete search history.

(56) References Cited

U.S. PATENT DOCUMENTS

| | | | |
|---|---|---|---|
| 7,468,276 B2 | 12/2008 | Hariri | |
| 2003/0087394 A1 | 5/2003 | Sharma | |
| 2003/0235563 A1 | 12/2003 | Strom | |
| 2004/0161419 A1 | 8/2004 | Strom | |
| 2005/0019865 A1 | 1/2005 | Kihm | |
| 2005/0032209 A1 | 2/2005 | Messina | |
| 2005/0037491 A1 | 2/2005 | Mistry | |
| 2005/0054093 A1 | 3/2005 | Haas | |
| 2005/0054098 A1 | 3/2005 | Mistry | |
| 2005/0058629 A1 | 3/2005 | Harmon | |
| 2005/0058631 A1 | 3/2005 | Kihm | |
| 2005/0124003 A1 | 6/2005 | Atala | |
| 2006/0078993 A1 | 4/2006 | Phan | |
| 2006/0153816 A1 | 7/2006 | Brown | |
| 2006/0153817 A1 | 7/2006 | Kihm | |
| 2006/0153818 A1 | 7/2006 | Dhanaraj | |
| 2006/0154366 A1 | 7/2006 | Brown | |
| 2006/0154367 A1 | 7/2006 | Kihm | |
| 2006/0166361 A1 | 7/2006 | Seyda | |
| 2006/0188983 A1 | 8/2006 | Harris | |
| 2006/0222634 A1* | 10/2006 | Clarke et al. ............. | 424/93.7 |
| 2006/0223177 A1 | 10/2006 | Harris | |
| 2006/0233765 A1 | 10/2006 | Messina | |
| 2006/0233766 A1 | 10/2006 | Messina | |
| 2006/0234376 A1 | 10/2006 | Mistry | |
| 2007/0009494 A1 | 1/2007 | Mistry | |
| 2007/0014771 A1 | 1/2007 | Mistry | |
| 2007/0015278 A1 | 1/2007 | Li | |
| 2007/0036767 A1 | 2/2007 | Mistry | |
| 2007/0190034 A1* | 8/2007 | Paludan et al. ........... | 424/93.7 |
| 2007/0275362 A1 | 11/2007 | Edinger | |
| 2008/0032401 A1 | 2/2008 | Edinger | |
| 2008/0131410 A1 | 6/2008 | Hariri | |
| 2008/0152629 A1 | 6/2008 | Edinger | |
| 2008/0226595 A1 | 9/2008 | Edinger | |

FOREIGN PATENT DOCUMENTS

WO    WO 00/73421 A2    6/2000

OTHER PUBLICATIONS

Guo et al, Stem Cells to Pancreatic-Cells: New Sources for Diabetes Cell Therapy, Endocrine Reviews 30(3):214-2274, 2009.*
Miki et al, Amnion-Derived Pluripotent/Multipotent Stem Cells, Stem Cell Reviews, 2006, pp. 133-141.*
Parolini, O., et al., Stem Cells 2008;26:300-311.
Heeger, P.S., Transplantation 2004;78:1411-12.
Bailo, M., et al., Transplantation 2004;78:1439-1448.
De Coppi, P., et al., Nature Biotechnology 2007;25:100-106.
Delo, D.M., et al., Methods in Enzymology 2006;419:426-438.
Dios, E., et al., Cornea 2005;24:182-188.
Hori, J., et al., Cornea 2006;25:S53-S58.
Houlihan, J.M., et al., The Journal of Immunology 1995;154:5664-5674.
Hunt, J.S., et al., The Journal of Immunology 1986;136:364-367.
Ishitani, A., et al., The Journal of Immunology 2003;1376-1384.
Kamiya, K., et al., Experimental Eye Research 2005;80:671-679.
Kubo, M., et al., Investigative Ophthalmology & Visual Science 2001;42:1539-1546.
Lefebvre, S., et al., Human Immunology 2000;61:1095-1101.
Li, H., et al., Investigative Ophthalmology & Visual Science 2005;46:900-907.
Miki, T., et al., Stem Cells 2005;23:1549-1559.
Miki, T., et al., Stem Cell Reviews 2006;2:133-142.
Petroff, M.G., Journal of Reproductive Immunology 2005;68:1-13.
Ueta, M., et al., Clinical Experimental Immunology 2002;129:464-470.
Wolbank, S., et al., Tissue Engineering 2007;13:1173-1183.
Hammer, A., et al., American Journal of Reproductive Immjunology 1997;37:161-171.

* cited by examiner

*Primary Examiner* — Maria Marvich
(74) *Attorney, Agent, or Firm* — Linda O. Palladino; Gail M. Kempler (57) ABSTRACT

The invention is directed to novel methods for modulating inflammatory and/or immune responses. Such methods utilize compositions comprising extraembryonic cells (herein referred to as EE cells) including but not limited to extraembryonic HLA-G positive cells (herein referred to as EHP cells) and amnion-derived multipotent progenitor cells (herein referred to as AMP cells); compositions comprising expanded EE cell populations, and/or cell lysates and/or conditioned media derived therefrom, alone or in combination with each other and/or in combination with various extracellular matrices and/or devices and/or other suitable active agents.

6 Claims, 2 Drawing Sheets

METHODS FOR MODULATING INFLAMMATORY AND/OR IMMUNE RESPONSES

CROSS-REFERENCE TO RELATED APPLICATIONS

This application claims priority under 35 USC §119(e) to U.S. Provisional Application No. 60/880,745, filed Jan. 17, 2007, U.S. Provisional Application No. 60/902,440, filed Feb. 21, 2007, U.S. Provisional Application No. 60/997,604, filed Oct. 4, 2007, the contents of which are incorporated herein by reference in their entirety.

STATEMENT REGARDING FEDERALLY SPONSORED RESEARCH OR DEVELOPMENT

This invention was made in part with United States government support awarded by the following agency: U.S. Army Medical Research Acquisition Activity, ERMS #06100002. The United States may have certain rights to this invention.

FIELD OF THE INVENTION

The field of the invention is directed to novel methods for modulating inflammatory and/or immune responses. Such methods utilize compositions comprising extraembryonic cells (herein referred to as EE cells) including but not limited to extraembryonic HLA-G positive cells (herein referred to as EHP cells) and amnion-derived multipotent progenitor cells (herein referred to as AMP cells); compositions comprising expanded EE cell populations, and/or cell lysates and/or conditioned media derived therefrom, alone or in combination with each other and/or in combination with various extracellular matrices and/or devices and/or other suitable active agents.

DESCRIPTION OF RELATED ART

U.S. Published Application No. 2006026337 (incorporated herein by reference) discloses the immunomodulatory properties of multipotent adult progenitor cells, called MAPCs, and uses thereof.

Ueta, M., et al., (Clin Exp Immunol 2002; 129:464-470) describe the immunosuppressive properties of decellularized amniotic membrane.

Klyushnenkova, E., et al., (Journal of Biomedical Science, 2005, 12:47-57) describe T cell responses to allogeneic human mesenchymal stem cells, called MSCs.

Williams, M. (Journal of Hematotherapy & Stem Cell Research, 2003, 12:757-758) discusses the functional expression of HLA-G and whether it can be exploited for successful stem cell transplantation and engraftment.

Götherström, C., et al., (The Hematology Journal, 2005, 90(8):1017-1026) disclose that adult bone marrow-derived mesenchymal stem cells do not express HLA-G protein.

BACKGROUND OF THE INVENTION

Stem cells have the remarkable potential to proliferate and differentiate into many different cell types in the body. Serving as a repair system for the body, they can theoretically divide without limit to replenish other cells throughout a person's life. When a stem cell divides, each new cell has the potential to either remain a stem cell or become another type of cell with a more specialized function, such as a muscle cell, a red blood cell, or a brain cell. Perhaps the most important potential application of human stem cells is the generation of cells and tissues that could be used for cell-based therapies. Examples of stem cell studies are provided (Tylki-Szymanska, A., et al., Journal of Inherited Metabolic Disease, 1985. 8(3): p. 101-4; Yeager, A. M., et al., American Journal of Medical Genetics, 1985. 22(2): p. 347-55; John, T., 2003. 16(1): p. 43-65, vi.).

Placental tissue is abundantly available as a discarded source of a many potentially useful cell types including a type of multipotent cell called placental-derived cells. Although discarded at parturition as part of the placental membranes, lineage analysis shows that, the epithelial layer of the amnion, from which such multipotent cells can be isolated, is uniquely descended from the epiblast in embryonic development. The epiblast contains the cells that will ultimately differentiate into the embryo and cells that will give rise to an extraembryonic tissue, the amnion. Thus far, only four cell types have been described in the literature as being pluripotent. These are the inner cell mass (ICM) of the pre-implantation embryo, which gives rise to the epiblast, the epiblast itself, embryonic stem (ES) and embryonic germ cells (EG). Thus, identification, purification and propagation of a multipotent cell population from discarded amnion tissue would provide an extremely valuable source of stem cells for replacement cell therapy.

With an average yield of over 200 million cells per placenta, large numbers of cells are available from this source. If these cells were to become useful cells for transplantation medicine, they could provide a nearly inexhaustible supply of starting material in every part of the world. No stem cell source provides such a large starting population of cells, and collection does not require an invasive or destructive procedure. Furthermore, there are no ethical, religious or social issues associated with these cells as the tissue is derived from the placenta.

Another important consideration in stem cell and organ transplant therapies is graft tolerance. In humans, the protein expression of the cell surface marker HLA-G was originally thought to be restricted to immune-privileged sites such as placenta, as well as related cells, including some isolated from amniotic fluid, placental macrophages, and cord blood, thus implicating its role in maternal-fetal tolerance (Urosevic, M. and Dummer, R. (2002) ASHI Quarterly; 3rd Quarter 2002:106-109). Additionally, studies involving heart-graft acceptance have suggested that the protein expression of HLA-G may enhance graft tolerance (Lila, N., et al. (2000) Lancet 355:2138; Lila, N. et al. (2002) Circulation 105:1949-1954). HLA-G protein is not expressed on the surface of undifferentiated or differentiated embryonic stem cells (Drukker, M, et al. (2002) PNAS 99(15):9864-9869). Thus, it is desirable that stems cells intended for cell-based therapies express HLA-G protein.

The transfer of living cells, tissues, or organs from a donor to a recipient, with the intention of maintaining the functional integrity of the transplanted material in the recipient defines transplantation. A major goal in solid organ transplantation is the permanent engraftment of the donor organ without a graft rejection immune response generated by the recipient, while preserving the immunocompetence of the recipient to respond to other foreign antigens. Typically, in order to prevent host rejection responses, nonspecific immunosuppressive agents such as cyclosporine, methotrexate, steroids and FK506 are used. These agents must be administered on a daily basis and if stopped, graft rejection usually results. Despite the use of immunosuppressive agents, chronic graft rejection still remains a major source of morbidity and mortality in human organ transplantation. Most human transplants fail within 10 years without permanent graft acceptance. Only 50% of heart transplants survive 5 years and 20% of kidney transplants survive 10 years (Opelz, et al., Lancet, 1:1223 (1981); Gjertson, UCLA Tissue Typing Laboratory, p. 225 (1992); Powles, Lancet, p. 327 (1980); and Ramsay, New Engl. J. Med., p. 392 (1982)).

Among the most prominent adverse reactions encountered as a result of transplant therapies are (i) the host versus graft response ("HVG") (rejection of the transplant by an immune competent host), and (ii) graft versus host disease ("GVHD") (which occurs primarily in an immunocompromised host when it is recognized as non-self by immunocompetent cells in the graft). Graft rejection in a host can be avoided by perfectly matching the donor and the host tissue. However, perfect matches are virtually non-existent (with the exception of identical twins). One potential way around this is the use of autologous (syngeneic) tissue. Unfortunately, the host tissue is often not suitable or was not collected prior to need. In fact, the need for the transplant therapy is frequently to replace damaged tissue in the host. This means that the use of autologus (syngeneic) tissue is not generally useful in practical applications.

Another option is matching an allogeneic donor and host as closely as possible using blood and/or tissue typing. Unfortunately, even the closest of matches does not prevent serious HVG, so allogeneic transplant therapies require immunosuppression and immunosuppressive drugs (see below).

Another approach to avoid HVG and its complications in transplant therapies is to disable the immune system of the recipient host. A draw back to such immunoablation or suppression is that it compromises the host's immune defenses such that the host is readily susceptible to infections, a major cause of morbidity and mortality among transplant patients. Compromising the host immune system also causes or exacerbates graft versus host disease ("GVHD"). GVHD occurs when donor tissue contains immunocompetent cells that recognize MHC proteins of the recipient as non-self. This activates T-cells called TH1 cells which in turn secrete pro-inflammatory cytokines, such as IL-2, interferon gamma, and TNF alpha, which trigger an immune attack on recipient targets including the skin, GI tract, liver, and lymphoid organs (Ferrara and Deeg, 1991). GVHD is particularly a problem in bone marrow transplants, where it has been shown to be mediated primarily by T lymphocytes (Grebe and Streilein, 1976).

A number of immunosuppressive drugs have been developed and are in use to prevent and/or treat these immune system dysfunctions. Unfortunately, none of the immunosuppressive drugs currently available are entirely effective and all of them have serious drawbacks and deleterious side effects. Glucocorticoids, which are used primarily to treat inflammation and inflammatory diseases, are known to be immunosuppressive and are considered be the best primary treatment for HVG and GVHD. They inhibit T-cell proliferation and T-cell-dependent immune responses. Drugs that act on immunophilins (i.e. cyclosporine, tacrolimus, sirolimus) can be effective in reducing adverse immune reactions in transplant patients, but they also weaken the immune system so much that patients are left highly vulnerable to infections. Cytostatics (i.e. methotrexate, azathiopine, mercatopurine, and cytotoxic antibiotics) are also widely used either alone or in combination with other drugs. They cause a variety of side effects, some of which can be deleterious to the patient. Antibodies (polyclonals and monoclonals such as anti-T-cell receptor (CD23) and anti-IL2 receptor (CD25) antibodies) have also been used. Many other drugs have also been used (i.e. interferon, opioids, TNF binding proteins, mycophenolate, and small biological agents such as FTY720). None of the immunosuppressive drugs, whether used alone or in combination with other agents, are fully effective and all of them generally leave patients still susceptible to HVG and GVHD and weaken their ability to defend against infection. Furthermore, all of these drugs cause serious side effects including gastrointestinal toxicity, nephrotoxicity, hypertension, myelosuppression, hepatotoxicity, and hypertension, to name a few.

Clearly, a more specific type of immune suppression without the drawbacks listed above would be ideal. For example, an agent that can suppress or eliminate alloreactive T-cells, specifically, would be effective against HVG and GVHD (at least for allogeneic grafts) without the negative side effects that occur with agents that generally attack and compromise the immune system. However, to date, no such agent(s) have been developed. Therefore, it is an object of the present invention to fulfill this unmet need.

SUMMARY OF THE INVENTION

In accordance with the present invention, Applicants have discovered that extraembryonic cells (EE cells) including but not limited to extraembryonic HLA-G positive cells (EHP cells) and amnion-derived multipotent progenitor cells (AMP cells), and/or cell lysates and/or conditioned media derived therefrom, alone or in combination with each other and/or other suitable active agents, are useful agents capable of suppressing, preventing, ameliorating or treating HVG, GVHD, as well as many other immune and/or inflammatory diseases and disorders. The cells of the present invention express HLA-G, do not express MHC Class II antigens, are telomerase negative, do not form teratomas, are not immortal, secrete cellular modulatory factors, and are readily available in great numbers.

It is an object of the instant invention to provide methods for modulating inflammatory and/or immune responses by administering EHP cells, and in particular, AMP cells. It is also an object of the instant invention to suppress, treat, prevent and/or ameliorate inflammatory, immune, and/or allergic diseases and disorders in a subject in need thereof by administering EHP cells, and in particular, AMP cells. It is a further object of the invention to provide methods for modulating inflammatory and/or immune responses and/or treating, preventing and/or ameliorating inflammatory, immune, and/or allergic diseases and disorders in a subject in need thereof by administering conditioned media derived from EHP cells, cell lysates derived therefrom, or cell products derived therefrom, each alone or in combination, including in combination with each other and/or other suitable active agents. It is a further object of the invention to provide methods for modulating inflammatory and/or immune responses and/or treating, preventing and/or ameliorating inflammatory, immune, and/or allergic diseases and disorders in a subject in need thereof by administering conditioned media derived from AMP cells, referred to herein as amnion-derived cytokine solution (ACCS), cell lysates derived therefrom, or cell products derived therefrom, each alone or in combination, including in combination with each other and/or in combination with various extracellular matrices and/or devices and/or other suitable active agents.

The phenotypical characterization of AMP cells reveals them to be ideal candidates for cellular therapy for immune-mediated diseases and disorders. As shown in the example below, in vitro data show AMP cells are not immunogenic and have immuno-modulatory properties. AMP cells down-regulate T cell responses to various stimuli, including mitogen responses, allo-antigen (MLR), and memory T cell responses. The mechanisms by which AMP cells may facilitate a down-regulated immuno-modulated environment may include several aspects. First, AMP cells up-regulate the expression of the programmed cell death ligands PD-L1 and PD-L2 when exposed to proinflammatory cytokines such as IFN-γ. These ligands may bind to their receptors (PD-1) on T cells, resulting in the down-regulation of activation and cytokine secretion. AMP cells are also positive for the expression of Fas antigen. This antigen can interact with Fas-ligand expressed on activated T cells and instigate cell death of these T cells. Finally, AMP cells have high expression of HLA-G surface antigen when exposed to IFN-γ and proinflammatory cytokines. In fact, AMP cells up-regulate HLA-G expression on their surface during culture in a MRL. HLA-G has been shown to have substantial immuno-modulatory functions, including impairment of proliferation of allo-specific T cells, inhibition of NK cell activity, tolerization of dendritic cells, and induction of T regulatory cells. As shown in the example below, AMP cells do not have immuno-modulatory effects on T cells when separated from these responding cells via transwell membranes. Thus, the mechanisms of action by AMP cells most likely involve cell-to-cell contact with responding immune mediating cells. These unique characteristics of AMP cells identify them as an ideal cellular therapy for afflictions involving immune-mediated mechanisms.

Accordingly, a first aspect of the invention is a method of suppressing, preventing or ameliorating an immune response in a subject in need thereof, such method comprising administering to the subject an effective amount of a composition selected from the group consisting of a composition comprising EHP cells, including AMP cells, conditioned media derived therefrom, cell lysates derived therefrom, and cell products derived therefrom, each alone or in combination with each other. In specific embodiments, the immune response to be suppressed, prevented or ameliorated is T cell activation, NK cell activation, downregulation of antigen presenting cell activation, or tolerization of dendritic cells to prevent T cell activation. In more specific embodiments, the antigen preventing cells are B cells, macrophages or monocytes.

In one embodiment, the immune response is an autoimmune response. In specific embodiments the autoimmune response is selected from the group consisting of Type I diabetes, multiple sclerosis, systemic lupus erythematosus, Grave's disease, autoimmune hemolytic anemia, bullous pemphigoid, Hashimoto's thyroiditis, myasthenia gravis, pemphigus, pernicious anemia, and the like.

In another embodiment the immune response is an allogeneic response. In a specific embodiment, the allogeneic response is selected from the group consisting of graft versus host disease and host versus graft disease.

A third aspect of the invention is a method of suppressing, preventing or ameliorating an inflammatory response in an subject in need thereof, such method comprising administering to the subject an effective amount of a composition selected from the group consisting of a composition comprising EHP cells, including AMP cells, conditioned media derived therefrom, cell lysates derived therefrom, and cell products derived therefrom, each alone or in combination with each other.

A fourth aspect of the invention is a method of ameliorating an inflammatory response in an subject in need thereof, such method comprising administering to the subject an effective amount of a composition selected from the group consisting of a composition comprising EHP cells, including AMP cells, conditioned media derived therefrom, cell lysates derived therefrom, and cell products derived therefrom, each alone or in combination with each other.

In another embodiment the inflammatory response is selected from the group consisting of inflammatory diseases of integument, inflammatory bowel diseases and rheumatic diseases. In specific embodiments the inflammatory diseases of the integument are selected from the group consisting of psoriasis and atopic dermatitis. In another specific embodiment the inflammatory bowel diseases are selected from the group consisting of ulcerative colitis and Crohn's disease. In yet another specific embodiment the rheumatic diseases are selected from the group consisting of osteoarthritis, rheumatoid arthritis, juvenile rheumatoid arthritis, fibromyalgia, scleroderma, spondyloarthropathies, gout, infectious arthritis, polymyalgia rheumatica, polymyositis, psoriatic arthritis, bursitis, tendinitis, CIAS1-related Autoinflammatory Periodic Syndromes (CAPS), pelvic inflammatory disease, interstitial cystitis, Henoh-Schonlein purpura, Behcet's syndrome and the like.

In a preferred embodiment of the invention the subject is a human or non-human animal.

In another embodiment the composition comprising EHP cells, including AMP cells, conditioned media derived therefrom, cell lysates derived therefrom, or cell products derived therefrom, each or in combination with each other, are administered topically, parenterally or enterally. In a preferred embodiment the EHP cells are AMP cells.

In a fifth aspect of the invention, composition of EHP cells, including AMP cells, conditioned media derived therefrom, cell lysates derived therefrom, or cell products derived therefrom, each alone or in combination with each other, is co-administered with one or more active agents. In one embodiment the active agent is selected from the group consisting of corticosteroids, cyclosporine, tacrolimus, sirolimus, methotrexate, azathiopine, mercatopurine, cytotoxic antibiotics, polyclonal antibodies, monoclonal antibodies, interferon, opioids, TNF binding proteins, mycophenolate, and FTY720. In a specific embodiment the monoclonal antibodies are selected from the group consisting of anti-T-cell receptor (CD23) and anti-IL2 receptor (CD25) antibodies In another embodiment the EHP cells, including AMP cells, conditioned media derived therefrom, cell lysates derived therefrom, or cell products derived therefrom, are allogeneic to the subject.

A sixth aspect of the invention is a method of preparing suppressor T-cells, wherein the method comprises the steps of contacting activated effector T-Cells with allogeneic EHP cells in culture to produce suppressor T-cells and separating the suppressor T-cells from the culture. In one specific embodiment, the EHP cells are AMP cells.

A seventh aspect of the invention is a method of reducing an immune response against an alloantigen, wherein the method comprises the steps of culturing activated T-cells with EHP cells in vitro, whereby the EHP cells induce the activated T-cells to become suppressor T-cells and contacting immune effector cells with the suppressor T-cells in an amount effective to reduce the immune response. In one embodiment the EHP cells are AMP cells. In another embodiment, the EHP cells, the T cells and the effector cells are human cells. In another embodiment, the effector cells are T-cells.

An eighth aspect of the invention is a method of treating a transplant recipient for graft versus host disease, wherein the method comprises the steps of culturing activated human T-cells with human EHP cells in vitro, whereby the human EHP cells induce the activated human T-cells to become human suppressor T-cells and treating the recipient of a donor transplant with the human suppressor T-cells in an amount effective to reduce an immune response against the recipient by the transplant. In a preferred embodiment, the EHP cells are AMP cells. In another embodiment, the suppressor T-cells are allogeneic to the EHP cells.

A ninth aspect of the invention is a method of reducing an immune response to a donor transplant, wherein the method comprises the steps of comprising culturing activated human T-cells with human EHP cells in vitro to produce human suppressor T-cells and administering to the recipient of the donor transplant the human suppressor T-cells in an amount effective to reduce an immune response in the recipient to the transplant. In a preferred embodiment the EHP cells are AMP cells. In another embodiment, the human EHP cells are allogeneic to the activated human T-cells. In another embodiment the suppressor T-cells are administered to the recipient prior to administration of the transplant. In another embodiment the suppressor T-cells are administered concurrently with administration of the transplant, and in yet another embodiment the suppressor T-cells are administered as part of the transplant, and in still another embodiment the suppressor T-cells are administered after the transplant.

Other features and advantages of the invention will be apparent from the accompanying description and the claims. The contents of all references, pending patent applications and published patents, cited throughout this application are hereby expressly incorporated by reference. In case of conflict, the present specification, including definitions, will control.

DEFINITIONS

As defined herein "isolated" refers to material removed from its original environment and is thus altered "by the hand of man" from its natural state.

As used herein, the term "protein marker" means any protein molecule characteristic of the plasma membrane of a cell or in some cases of a specific cell type.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning. Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cell types.

As used herein, the term "extraembryonic tissue" means tissue located outside the embryonic body which is involved with the embryo's protection, nutrition, waste removal, etc. Extraembryonic tissue is discarded at birth. Extraembryonic tissue includes but is not limited to the amnion, chorion (trophoblast and extraembryonic mesoderm including umbilical cord and vessels), yolk sac, allantois and amniotic fluid (including all components contained therein). Extraembryonic tissue and cells derived therefrom have the same genotype as the developing embryo.

As used herein, the term "extraembryonic cells" or "EE cells" means a population of cells derived from the extraembryonic tissue.

As used herein, the term "EHP cells" means a population of cells derived from the extraembryonic tissue which have the characteristics of being HLA-G positive upon isolation, are MHC Class II negative, do not express the co-stimulatory molecules CD80 and CD86 and are not MAPCs as described in US Published Patent Application No. 20060263337.

As used herein, the term "amnion-derived multipotent progenitor cell" or "AMP cell" means a population of epithelial cells that are derived from the amnion. In addition to the characteristics described above for EHP cells, AMP cells grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated AMP cells will not react with antibodies to the stem/progenitor cell markers c-kit and Thy-1. Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172:493-500). However, the methods used herein provide improved compositions and populations of cells. AMP cells have previously been described as "amnion-derived cells" (see U.S. Provisional Application Nos. 60/666,949, 60/699,257, 60/742,067, U.S. Provisional Application Nos. 60/813,759, U.S. application Ser. No. 11/333,849, U.S. application Ser. No. 11/392,892, and PCTUS06/011392, each of which is incorporated herein in its entirety).

The term "composition of extraembryonic cells" as used herein includes the cells and compositions described in this application and in US2003/0235563, US2004/0161419, US2005/0124003, U.S. Provisional Application Nos. 60/666,949, 60/699,257, 60/742,067, 60/813,759, U.S. application Ser. No. 11/333,849, U.S. application Ser. No. 11/392,892, PCTUS06/011392, US2006/0078993, PCT/US00/40052, U.S. Pat. No. 7,045,148, US2004/0048372, and US2003/0032179, the contents of which are incorporated herein by reference in their entirety.

By the term "animal-free" when referring to compositions, growth conditions, culture media, etc. described herein, is meant that no animal-derived materials, such as animal-derived serum, other than human materials, such as native or recombinantly produced human proteins, are used in the preparation, growth, culturing, expansion, or formulation of the composition or process.

By the term "expanded", in reference to EHP cell compositions, means that the EHP cell population constitutes a significantly higher concentration of cells than is obtained using previous methods. For example, the level of cells per gram of amniotic tissue in expanded compositions of AMP cells is at least 50 and up to 150 fold higher than the number of cells in the primary culture after 5 passages, as compared to about a 20 fold increase in such cells using previous methods. In another example, the level of cells per gram of amniotic tissue in expanded compositions of AMP cells is at least 30 and up to 100 fold higher than the number of cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the EHP cells. As used herein "passage" or "passaging" refers to subculturing of cells. For example, cells isolated from the amnion are referred to as primary cells. Such cells are expanded in culture by being grown in the growth medium described herein. When such primary cells are subcultured, each round of subculturing is referred to as a passage. As used herein, "primary culture" means the freshly isolated EHP cell population.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium. Examples of methods of preparing conditioned media are described in U.S. Pat. No. 6,372,494 which is incorporated by reference in its entirety herein. As used herein, conditioned medium also refers to components, such as proteins, that are recovered and/or purified from conditioned medium or from EHP cells including AMP cells.

As used herein, the term "amnion-derived cellular cytokine solution" or "ACCS" means conditioned medium that has been derived from AMP cells or expanded AMP cells. ACCS has previously been referred to as "amnion-derived cellular cytokine suspension".

As used herein, "specific activity" means the specific activity of EHP cells, including AMP cells, and is determined by calculating a 50% inhibition dosage ($ID_{50}$). For example, using a standard allogeneic-antigen MLR, the 100% response is calculated by determining the PBMC responder response to the mismatched stimulator without addition of AMP cells. Then, AMP cells are titered into the MLR at 1:2 serial dilutions. The number of AMP cells required to half the 100% response is reported as the $ID_{50}$.

The term "lysate" as used herein refers to the composition obtained when cells, for example, EHP cells, are lysed and optionally the cellular debris (e.g., cellular membranes) is removed. This may be achieved by mechanical means, by freezing and thawing, by use of detergents, such as EDTA, or by enzymatic digestion using, for example, hyaluronidase, dispase, proteases, and nucleases.

As used herein, the term "substrate" means a defined coating on a surface that cells attach to, grown on, and/or migrate on. As used herein, the term "matrix" means a substance that cells grow in or on that may or may not be defined in its components. The matrix includes both biological and non-biological substances. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions.

The term "cell product" or "cell products" as used herein refers to any and all substances made by and secreted from a cell, including but not limited to, protein factors (i.e. growth factors, differentiation factors, engraftment factors, cytokines, morphogens, proteases (i.e. to promote endogenous cell delamination, protease inhibitors), extracellular matrix components (i.e. fibronectin, etc.).

The term "transplantation" refers to the administration of a composition either in an undifferentiated, partially differentiated, or fully differentiated form into a human or other animal.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents. As used herein, the term "syngeneic" means genetically identical members of the same species.

As used herein, the term "allogeneic" means variation in alleles among members of the same species.

As used herein, the terms "immunosuppressive drugs" or "immunosuppressants" are drugs that are used in immunosuppressive therapy to inhibit or prevent activity of the immune system.

As used herein, the term "GVHD" refers to graft versus host disease, which means the processes that occur primarily in an immunocompromised host when it is recognized as non-self by immunocompetent cells of a graft.

As used herein, the term "HVG" refers to host versus graft response, which means the processes which occur when a host rejects a graft. Typically, HVG is triggered when a graft is recognized as foreign (non-self) by immunocompetent cells of the host.

As used herein, the terms "inflammation" or "inflammatory response" means the reaction that occurs in the affected cells and adjacent tissues in response to an injury or abnormal stimulation caused by a physical, chemical, or biologic substance.

As used herein, the term "immune response" means the cells, tissues and protein factors (i.e. cytokines) involved in recognizing and attacking foreign substances within the body of an animal.

As used herein, the term "pharmaceutically acceptable" means that the components, in addition to the therapeutic agent, comprising the formulation, are suitable for administration to the patient being treated in accordance with the present invention.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

As used herein "subject" may mean either a human or non-human animal.

As used herein, the term "tissue" refers to an aggregation of similarly specialized cells united in the performance of a particular function.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual".

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Therapeutic Applications

It has been found that relatively small amounts of EHP cells can suppress inflammatory and immune responses. Accordingly, in certain aspects of the invention, certain embodiments provide compositions and methods for treating, ameliorating, and/or preventing or eliminating, adverse immune responses, such as those that occur in transplantation therapies. The low immunogenicity of allogeneic EHP cells, their ability to suppress adverse inflammatory and immune responses, and their high specific activity (as defined in the definitions and elsewhere herein) makes them particularly valuable for adjunctive therapies in the treatment of such diseases. EHP cells also are useful as immunosuppressive adjunctive therapeutics for treating adverse immune responses that occur in transplantation therapy (i.e. HVG and GVHD). Other immune disorders and diseases are discussed in more detail elsewhere herein. EHP cells further can be useful in adjunctive immunosuppressive therapy in the treatment of certain inflammatory diseases. Such diseases are discussed in greater detail below and elsewhere in the specification. It should be noted that the diseases and conditions discussed below are intended to be examples of suitable diseases and conditions which may be treated by the methods of the invention. Skilled artisans will recognize that treatment of many other related diseases and conditions are also contemplated by the methods of the invention.

Using the methods described herein for EHP cell isolation, characterization, and expansion, together with the disclosure herein on the immune-suppressing properties of EHP cells, EHP cells can be used to prevent, suppress, or diminish immune disorders, dysfunctions, or diseases, including, for example, adverse immune reactions, such as those that result from other therapies, including those that complicate transplantation therapies, such as HVG and GVHD. Such disorders, dysfunctions, and diseases also include congenital immune disorders and autoimmune diseases, among others. EHP cells are useful as both a primary and adjunctive therapeutic agent. EHP cells can be used therapeutically alone or together with other agents; can be administered before, during, and/or after such agents; used alone or with other agents; can be administered before, during, and/or after a transplant. If administered during transplant, EHP cells can be administered together with the transplant material or separately. If separately administered, the EHP cells can be administered sequentially or simultaneously with the transplant. Furthermore, EHP cells may be administered in advance of the transplant and/or after the transplant. Other agents that can be used in conjunction with EHP cells, in transplantation therapies in particular, include immunomodulatory agents. A variety of such agents are described elsewhere herein. In certain embodiments of the invention, the immunomodulatory agents are immunosuppressive agents, such as those described elsewhere herein.

In certain embodiments the EHP cells are administered by injection, such as by intravenous injection; are encapsulated for administration; are administered in situ (i.e. solid organ transplantation and organ repair). These and other forms of administration are discussed in detail elsewhere herein. In some embodiments of the invention, EHP cells are administered in doses measured by the ratio of EHP cells (cells) to body mass (weight). Alternatively, they can be administered in doses of a fixed number of cells. Dosing, routes of administration, formulations, and the like are discussed in greater detail elsewhere herein.

Because of their novel immunomodulatory properties, EHP cells, including AMP cells, conditioned media derived therefrom, cell lysates derived therefrom, or cell products derived therefrom, each alone or in combination, or in combination with other active agents, are particularly useful in the prevention and/or the amelioration of inflammatory and/or immune responses and/or allergic reactions. Inflammatory responses are characterized by dilation of blood vessels in the affected area resulting in increased blood flow to the area. If at the surface, it makes skin look red and feel warm. Capillaries in the area become more permeable allowing fluid to seep into the surrounding tissue resulting in edematous swelling around the infected site. The swelling and the effects of some of the chemicals released results in pain. Hence clinical characteristics of the inflammatory response are known as redness, heat, edema and pain. The inflammatory response occurs as a result of chemical messages produced by "mediators". There are two major classes of mediators: 1) cell-derived mediators which are produced by leukocytes and 2) plasma-derived mediators which are found in the blood plasma. Cell-derived mediators include arachidonic acid derivatives (i.e. prostaglandins and leukotrines), cytokines, lymphokines and monokines, interleukin, platelet activating factor (PAF), histamine and bradykinin. Plasma-derived mediators include complement and interferons. Inflammatory responses may be genetic in nature (i.e. CAPS, see below for details). They may be environmentally induced or virally induced. Non-limiting examples of diseases having inflammatory responses which are suitable for treatment with EHP cells, including AMP cells, conditioned media derived therefrom, cell lysates derived therefrom, or cell products derived therefrom, each alone or in combination, including in combination with other active agents, include the following:

Inflammatory Diseases of Integument which include psoriasis and eczema (i.e. atopic dermatitis). Psoriasis is an inflammatory skin condition. There are five types, each with unique signs and symptoms. Between 10% and 30% of people who develop psoriasis get a related form of arthritis called "psoriatic arthritis," which causes inflammation of the joints. Plaque psoriasis is the most common type of psoriasis. About 80% of people who develop psoriasis have plaque psoriasis, which appears as patches of raised, reddish skin covered by silvery-white scale. These patches, or plaques, frequently form on the elbows, knees, lower back, and scalp. However, they can occur anywhere on the body. The other types are guttate psoriasis (small, red spots on the skin), pustular psoriasis (white pustules surrounded by red skin), inverse psoriasis (smooth, red lesions form in skin folds), and erythrodermic psoriasis (widespread redness, severe itching, and pain). Regardless of type, psoriasis usually causes discomfort. The skin often itches, and it may crack and bleed. In severe cases, the itching and discomfort may keep a person awake at night, and the pain can make everyday tasks difficult. Psoriasis is a chronic, meaning lifelong, condition because there is currently no cure. People often experience flares and remissions throughout their life. Controlling the signs and symptoms typically requires lifelong therapy. Eczema is a general term encompassing various inflamed skin conditions. One of the most common forms of eczema is atopic dermatitis. Approximately 10-20% of the world population is affected by this chronic, relapsing, and very itchy rash at some point during childhood. Fortunately, many children with eczema find that the disease clears and often disappears with age. In general, atopic dermatitis will come and go, often based on external factors. Although its cause is unknown, the condition appears to be an abnormal response of the body's immune system. In people with eczema, the inflammatory response to irritating substances overacts, causing itching and scratching. Eczema is not contagious and, like many diseases, currently cannot be cured. However, for most patients the condition may be managed well with treatment and avoidance of triggers.

Inflammatory Bowel Diseases (IBDs) are chronic inflammatory diseases of the GI tract of unknown etiology, and include ulcerative colitis (UC) and Crohn's disease (CD), which is also referred to as regional enteritis, terminal ileitis, or granulomatous ileocolitis. Ulcerative colitis is an inflammatory disease of the large intestine, also called the colon. In ulcerative colitis, the inner lining (mucosa) of the intestine becomes inflamed and develops ulcers (an ulcer is a sore, which means it's an open, painful wound). Ulcerative colitis is often the most severe in the rectal area, which can cause frequent diarrhea. Mucus and blood often appear in the stool if the lining of the colon is damaged. Crohn's disease differs from ulcerative colitis in the areas of the bowel it involves—it most commonly affects the last part of the small intestine called the terminal ileum and parts of the large intestine. However, Crohn's disease isn't limited to these areas and can attack any part of the digestive tract. Crohn's disease causes inflammation that extends much deeper into the layers of the intestinal wall than ulcerative colitis does. Crohn's disease generally tends to involve the entire bowel wall, whereas ulcerative colitis affects only the lining of the bowel.

Rheumatic Diseases encompass many diseases including:

Osteoarthritis—This is the most common type of arthritis, affecting an estimated 21 million adults in the United States. Osteoarthritis primarily affects cartilage, which is the tissue that cushions the ends of bones within the joint. In osteoarthritis, the cartilage begins to fray and may entirely wear away. Osteoarthritis can cause joint pain and stiffness. Disability results most often when the disease affects the spine and the weight-bearing joints (the knees and hips).

Rheumatoid arthritis—This inflammatory disease of the synovium, or lining of the joint, results in pain, stiffness, swelling, joint damage, and loss of function of the joints. Inflammation most often affects joints of the hands and feet and tends to be symmetrical (occurring equally on both sides of the body). This symmetry helps distinguish rheumatoid arthritis from other forms of the disease. About 1 percent of the U.S. population (about 2.1 million people) has rheumatoid arthritis.

Juvenile rheumatoid arthritis—This is the most common form of arthritis in childhood, causing pain, stiffness, swelling, and loss of function of the joints. The arthritis may be associated with rashes or fevers, and may affect various parts of the body.

Fibromyalgia—Fibromyalgia is a chronic disorder that causes pain throughout the tissues that support and move the bones and joints. Pain, stiffness, and localized tender points occur in the muscles and tendons, particularly those of the neck, spine, shoulders, and hips. Patients may also experience fatigue and sleep disturbances.

Scleroderma—Also known as systemic sclerosis, scleroderma means literally "hard skin." The disease affects the skin, blood vessels, and joints. It may also affect internal organs, such as the lungs and kidneys. In scleroderma, there is an abnormal and excessive production of collagen (a fiber-like protein) in the skin or internal organs.

Spondyloarthropathies—This group of rheumatic diseases principally affects the spine. One common form—ankylosing spondylitis—not only affects the spine, but may also affect the hips, shoulders, and knees as the tendons and ligaments around the bones and joints become inflamed, resulting in pain and stiffness. Ankylosing spondylitis tends to affect people in late adolescence or early adulthood. Reactive arthritis, sometimes called Reiter's syndrome, is another spondyloarthropathy. It develops after an infection involving the lower urinary tract, bowel, or other organ and is commonly associated with eye problems, skin rashes, and mouth sores.

Gout—This type of arthritis results from deposits of needle-like crystals of uric acid in the joints. The crystals cause inflammation, swelling, and pain in the affected joint, which is often the big toe.

Infectious arthritis—This is a general term used to describe forms of arthritis that are caused by infectious agents, such as bacteria or viruses. Parvovirus arthritis and gonococcal arthritis are examples of infectious arthritis. Arthritis symptoms may also occur in Lyme disease, which is caused by a bacterial infection following the bite of certain ticks. In those cases of arthritis caused by bacteria, early diagnosis and treatment with antibiotics are crucial to get rid of the infection and minimize damage to the joints.

Polymyalgia rheumatica—Because this disease involves tendons, muscles, ligaments, and tissues around the joint, symptoms often include pain, aching, and morning stiffness in the shoulders, hips, neck, and lower back. It is sometimes the first sign of giant cell arteritis, a disease of the arteries characterized by inflammation, weakness, weight loss, and fever.

Polymyositis—This is a rheumatic disease that causes inflammation and weakness in the muscles. The disease may affect the whole body and cause disability.

Psoriatic arthritis—This form of arthritis occurs in some patients with psoriasis, a scaling skin disorder. Psoriatic arthritis often affects the joints at the ends of the fingers and toes and is accompanied by changes in the fingernails and toenails. Back pain may occur if the spine is involved.

Bursitis—This condition involves inflammation of the bursae, small, fluid-filled sacs that help reduce friction between bones and other moving structures in the joints. The inflammation may result from arthritis in the joint or injury or infection of the bursae. Bursitis produces pain and tenderness and may limit the movement of nearby joints.

Tendinitis (Tendonitis)—This condition refers to inflammation of tendons (tough cords of tissue that connect muscle to bone) caused by overuse, injury, or a rheumatic condition. Tendinitis produces pain and tenderness and may restrict movement of nearby joints.

Pelvic inflammatory disease (PID)—Is a general term that refers to infection and inflammation of the upper genital tract in women. It can affect the uterus (womb), fallopian tubes (tubes that carry eggs from the ovaries to the uterus), ovaries, and other organs related to reproduction. The scarring that results on these organs can lead to infertility, tubal (ectopic) pregnancy, chronic pelvic pain, abscesses (sores containing pus), and other serious problems. PID is the most common preventable cause of infertility in the United States.

CIAS1-related Autoinflammatory Periodic Syndromes (CAPS)—is a spectrum of rare inherited inflammatory conditions, including Familial Cold Autoinflammatory Syndrome (FCAS), Muckle-Wells Syndrome (MWS), and Neonatal Onset Multisystem Inflammatory Disease (NOMID). These syndromes are characterized by spontaneous systemic inflammation and are termed autoinflammatory disorders. A novel feature of these conditions (particularly FCAS and MWS) is that exposure to mild degrees of cold temperature can provoke a major inflammatory episode that occurs within hours. CAPS are caused by a range of mutations in the gene CIAS1 (also known as NALP3)

Miscellaneous inflammatory diseases include interstitial cystitis, Henoh-Schonlein purpura, and Behcet's syndrome.

Non-limiting examples of diseases having immune responses which are suitable for treatment with EHP cells, including AMP cells, conditioned media derived therefrom, cell lysates derived therefrom, or cell products derived therefrom, each alone or in combination, including in combination with other active agents, include:

GVHD refers to graft versus host disease, which means the processes that occur primarily in an immunocompromised host when it is recognized as non-self by immunocompetent cells of a graft.

HVG refers to host versus graft response, which means the processes which occur when a host rejects a graft. Typically, HVG is triggered when a graft is recognized as foreign (non-self) by immunocompetent cells of the host.

Juvenile (Type I) Diabetes is caused when the body forms antibodies that attack the beta cells in the islets of Langerhans in the pancreas. Since the beta cells are responsible for producing insulin, Type I diabetics must inject themselves with insulin their entire life.

Systemic lupus erythematosus (also known as lupus or SLE) is an autoimmune disease in which the immune system harms the body's own healthy cells and tissues. This can result in inflammation of and damage to the joints, skin, kidneys, heart, lungs, blood vessels, and brain.

Graves' disease is caused by an abnormal immune system response that attacks the thyroid gland, and causes too much production of thyroid hormones. Risk factors are being a woman over 20 years old, although the disorder may occur at any age and may affect men as well.

Miscellaneous immune disorders include autoimmune hemolytic anemia, bullous pemphigoid, Hashimoto's thyroiditis, myasthenia gravis, pemphigus, and pernicious anemia.

Allergic reactions are sensitivities to a specific substance, called an allergen, which is contacted through the skin, inhaled into the lungs, swallowed, or injected. Allergic reactions vary. They can be mild or serious. They can be confined to a small area of the body or may affect the entire body. Most occur within seconds or minutes after exposure to the allergen, but some can occur after several hours, particularly if the allergen causes a reaction after it is partially digested. In very rare cases, reactions develop after 24 hours. Anaphylaxis is a sudden and severe allergic reaction that occurs within minutes of exposure. Immediate medical attention is needed for this condition. It can get worse very, very fast and lead to death within 15 minutes if treatment is not received.

General Approaches For Transplantation/Cell-Based Therapies

One of skill in the art will recognize that HLA-G expression by cells is important in a cell's ability to evade immunosurveillance. Therefore, any cell that expresses HLA-G is potentially useful in practicing the methods of the invention. So, in addition to EHP cells and AMP cells, this includes cells such as certain tumor cells (see, for example, Tripathi, P. and Agrawal, S., Cancer Invest 2006, 24(2):178-186; Blaschitz, A., et al., Human Immunology 2000, 61:1074-1085), certain cells in the thymus (see, for example, Mallet, V., et al., Int Immunol 1999, 11:889-898; Mallet, V., et al., Reprod Immunol 1999, 43(2):225-234) and non-progenitor placental-derived HLA-G positive cells (Blaschitz, A., et al., Human Immunology 2000, 61:1074-1085).

Isolation, Identification and Characterization of EHP Cells

Various methods for isolating cells from the extraembryonic tissue, which may then be used to produce the EHP cells of the instant invention are described in the art (see, for example, US2003/0235563, US2004/0161419, US2005/0124003, U.S. Provisional Application Nos. 60/666,949, 60/699,257, 60/742,067, 60/813,759, U.S. application Ser. No. 11/333,849, U.S. application Ser. No. 11/392,892, PCTUS06/011392, US2006/0078993, PCT/US00/40052, U.S. Pat. No. 7,045,148, US2004/0048372, and US2003/0032179).

Identifying EHP cells—Once EE cells are isolated, it is necessary to identify which cells have the characteristics associated with EHP cells. For example, the cells are tested for the presence of HLA-G, the absence of MHC Class II antigens, and the absence of co-stimulatory molecules CD80 and CD86.

Isolation, Identification and Characterization of AMP Cells

In accordance with the invention, AMP cell compositions are prepared using the steps of a) recovery of the amnion from the placenta, b) dissociation of the cells from the amniotic membrane, c) culturing of the cells in a basal medium with the addition of a naturally derived or recombinantly produced human protein; and optionally d) further proliferation of the cells using additional additives and/or growth factors. Details are contained in US Publication No. 2006-0222634-A1, which is incorporated herein by reference.

The AMP cells of the invention are characterized as follows: Using commercially available antibodies to known stem cell markers, freshly isolated AMP cells have been extensively characterized. Briefly, freshly isolated AMP cells are substantially negative with respect to CD90 and CD117. In addition, such cell populations are essentially negative for protein expression of CD34, CD44, CD45, CD140b, CD105; essentially positive for protein expression of CD9 and CD29; between about 70-95% positive for protein expression of SSEA4, CD10, CD166 and CD227; between about 60-95% positive for protein expression of HLA-G, EGFR and CD26; and between about 10-50% positive for protein expression of CD71. Details on this procedure are contained in US Publication No. 2006-0222634-A1, which is incorporated herein by reference.

In alternative embodiments substantially purified AMP cell populations can be created using antibodies against protein markers expressed (positive selection) or not expressed (negative selection) on the cell surface of the AMP cells. These antibodies may be used to identify, characterize, isolate or create such substantially purified populations of AMP cells expressing those protein markers using a variety of methods. Details on this procedure are contained in US Publication No. 2006-0222634-A1, which is incorporated herein by reference.

In addition, protein markers that are not expressed on the surface of AMP cells may also be used to identify, isolate or create populations of AMP cells not expressing those markers. Such procedures may involve a negative selection method, such as passage of sample cells over a column containing anti-protein marker antibodies or by binding of cells to magnetic bead-conjugated antibodies to the protein markers or by panning on plates coated with protein marker antibodies and collecting the unbound cells. Alternatively, a single-cell suspension may be exposed to one or more fluorescent-labeled antibodies that immuno-specifically bind to the protein markers. Details on this procedure are contained in US Publication No. 2006-0222634-A1, which is incorporated herein by reference.

Expanded Populations of EHP Cells, Including AMP Cells

One of skill in the art will recognize that any of the EHP cells of the instant invention may be expanded using the methods described below for AMP cells.

As described herein and in US Publication No. 2006-0222634-A1, which is incorporated herein by reference, Applicants have discovered a novel method for isolation and propagation of multipotent AMP cells. Such methods result in AMP cell compositions which are expanded for multipotent cells, thereby providing, for the first time, sufficient quantities of cells to enable therapeutic cell transplantation. Expanded AMP cell compositions, which are made in accordance with the subject invention, are compositions in which the level of cells per gram of amniotic tissue is at least 50 fold and up to 150 fold higher after 5 passages, as compared to about 20 fold using previous methods. Alternatively, expanded AMP cell compositions, which are made in accordance with the subject invention, are compositions in which the level of cells per gram of amniotic tissue is at least 30 fold and up to 100 fold higher after 3 passages.

Additionally, the methods used for cell culture and proliferation provide a means to culture the cells, as well as other cells including but not limited to multipotent, pluripotent cells or totipotent cells, including, but not limited to, embryonic stem cells, in an animal-free system. Furthermore, the culture conditions described provide a cell that is less dependent on attachment to a culture surface for viability, thus allowing for propagation of the cells using suspension culture for efficient scale-up. Details on this procedure are contained in US Publication No. 2006-0222634-A1, which is incorporated herein by reference.

The expanded AMP cell compositions described herein demonstrate extensive proliferative potential, express certain genes known to be expressed only in undifferentiated cells (i.e. Nanog and Oct-4) and can differentiate into cell types that normally arise from all three embryonic germ layers (endoderm, ectoderm and mesoderm). This differentiation potential suggests that these expanded AMP cells may be able to contribute to a variety of cell types. The AMP cell compositions described herein are also useful as feeder layers for the growth of a variety of cell types, including but not limited to embryonic stem cells (ES cells). AMP cells, including those described herein, also produce a wide variety of cytokines and growth factors, thereby making both the cell compositions, conditioned media derived from the cells (ACCS), cell lysates therefrom, extracellular matrices produced by the cells, and combinations thereof useful for a variety of therapeutic applications, in particular cell-based therapeutic applications such as transplantation therapies.

In addition, the novel immunomodulating properties possessed by the compositions of the invention and described herein make the compositions useful in clinical settings in which modulating inflammatory and/or immune responses and/or treating, preventing and/or ameliorating inflammatory, immune, and/or allergic diseases and disorders in a subject in need thereof is indicated. Such uses are accomplished by administering EHP cells, including AMP cells, conditioned media derived therefrom, cell lysates derived therefrom, and cell products derived therefrom, each alone or in combination, including in combination with each other and/or other suitable active agents. Further details on the therapeutic potential of these cells and cell products are contained in US Publication No. 2006-0222634-A1, which is incorporated herein by reference.

Compositions—The compositions of the invention include substantially purified populations of EHP cells, including AMP cells, as well as cell lysates and/or conditioned media derived therefrom, alone or in combination with each other and/or other suitable active agents, and pharmaceutical compositions of such. The compositions of the invention can be prepared in a variety of ways depending on the intended use of the compositions. For example, a composition useful in practicing the invention may be a liquid comprising an agent of the invention, i.e. a substantially purified population of EHP cells, in solution, in suspension, or both (solution/suspension). The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment, salve, cream, or the like.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and muco-adhesive. Furthermore, the compositions may be combined with one or more active agents. Such other active agents include but are not limited to immunosuppressive agents such as cyclosporine, methotrexate, FK-506, corticosteroids and the like (see below).

Pharmaceutical Compositions—The present invention provides pharmaceutical compositions of substantially purified populations of EHP cells, including AMP cells, as well as cell lysates and/or conditioned media derived therefrom, alone or in combination with each other and/or other suitable active agents, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, and still others are familiar to skilled artisans.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Furthermore, the pharmaceuticals compositions may be combined with one or more active agents. Such other active agents include but are not limited to immunosuppressive agents such as cyclosporine, methotrexate, FK-506, corticosteroids and the like (see below).

Treatment Kits—The invention also provides for an article of manufacture comprising packaging material and a pharmaceutical composition of the invention contained within the packaging material, wherein the pharmaceutical composition comprises a substantially purified population of EHP cells, including AMP cells, as well cell lysates and/or conditioned media derived therefrom, alone or in combination with each other, and optionally in combination with other active agents and wherein the packaging material comprises a label or package insert which indicates that the substantially purified population of EHP cells including AMP cells, as well cell lysates and/or conditioned media derived therefrom, alone or in combination with each other can be used for treating a variety of disorders including but not limited to HVG, GVHD, and other inflammatory and immune diseases and disorders, allergic reactions, etc.

EHP cells, including AMP cells, as well cell lysates and/or conditioned media derived therefrom, alone or in combination with each other, are useful both as primary and adjunctive therapeutic agents and modalities. Such compositions can be used therapeutically alone or together with other agents. Such compositions can be administered before, during, and/or after such agents. Likewise, whether used alone or with other agents, such compositions can be administered before, during, and/or after a transplant or other cell-based therapy. If administered during transplant or other cell-based therapy, the compositions can be administered together with the transplant or other cell-based therapy material, or administered separately. If separately administered, the compositions can be administered sequentially or simultaneously with the transplant or other cell-based therapy. Furthermore, the compositions may be administered in advance of the transplant or other cell-based therapy and/or after the transplant or other cell-based therapy. In addition, the compositions maybe administered as the transplant. In such situations, they may be administered alone or in combination with other active agents, etc.

Other Agents Useful for Co-Administration.

EHP cells, including AMP cells, conditioned media derived therefrom, cell lysates derived therefrom, or cell products derived therefrom, each alone or in combination may be administered with other pharmaceutically active agents. In some embodiments one or more of such agents are formulated together with the compositions for administration. In some other embodiments the compositions and the one or more agents are in separate formulations. In yet some other embodiments the compositions comprising the EHP cells, including AMP cells, conditioned media derived therefrom, cell lysates derived therefrom, or cell products derived therefrom, each alone or in combination and/or the one or more agents are formulated with regard to adjunctive use with one another.

EHP cells, including AMP cells, conditioned media derived therefrom, cell lysates derived therefrom, or cell products derived therefrom, each alone or in combination, may be administered in a formulation comprising a immunosuppressive agents, such as any combination of any number of corticosteroids (i.e. glucocorticoids), cyclosporine, tacrolimus, sirolimus, methotrexate, azathiopine, mercatopurine, cytotoxic antibiotics, polyclonal and monoclonal antibodies such as anti-T-cell receptor (CD23) and anti-IL2 receptor (CD25) antibodies, interferon, opioids, TNF binding proteins, mycophenolate, and small biological agents such as FTY720. Immunosuppressive agents in accordance with the foregoing may be the only such additional agents or may be combined with other agents.

Such agents also include antibiotic agents, antifungal agents, and antiviral agents, to name just a few other pharmacologically active substances and compositions that may be used in accordance with embodiments of the invention. Typical antibiotics or anti-mycotic compounds include, but are not limited to, penicillin, streptomycin, amphotericin, ampicillin, gentamicin, kanamycin, mycophenolic acid, nalidixic acid, neomycin, nystatin, paromomycin, polymyxin, puromycin, rifampicin, spectinomycin, tetracycline, tylosin, zeocin, and cephalosporins, aminoglycosides, and echinocandins.

Additional agents may be used in conjunction with the EHP cells, including AMP cells of the present invention, to target the cells to a particular site, such as one of immune disorder, dysfunction, or disease, where they might be needed. Such agents may include growth factors and trophic signaling agents, such as cytokines. They may be used to attract EHP cells to therapeutically targeted sites. They may be administered to a subject prior to treatment with EHP cells, together with EHP cells, or after EHP cells are administered. Certain cytokines, for instance, alter or affect the migration of EHP cells or cells differentiated therefrom to sites in need of therapy, such as immunocompromised sites. Cytokines that may be used include, but are not limited to, stromal cell derived factor-1 (SDF-1), stem cell factor (SCF), angiopoietin-1, placenta-derived growth factor (PlGF), granulocyte-colony stimulating factor (G-CSF), cytokines that stimulate expression of endothelial adhesion molecules such as ICAMs and VCAMs, and cytokines that engender or facilitate targeting. They may be administered to a subject as a pre-treatment, along with EHP cells, including AMP cells, or after the compositions have been administered, to promote migration to desired sites and to achieve improved therapeutic effect. Such factors may be combined with EHP cells, including AMP cells, alone or in combination in a formulation suitable for them to be administered together. Alternatively, such factors may be formulated and administered separately.

Order of administration, formulations, doses, frequency of dosing, and routes of administration of factors (such as the cytokines) and EHP cells, including AMP cells, conditioned media derived therefrom, cell lysates derived therefrom, or cell products derived therefrom, each alone or in combination, generally will vary with the disorder or disease being treated, its severity, the subject, other therapies that are being administered, the stage of the disorder or disease, and prognostic factors, among others. General regimens that have been established for other treatments provide a framework for determining appropriate dosing in EHP cell-mediated direct or adjunctive therapy. These, together with the additional information provided herein, will enable the skilled artisan to determine appropriate administration procedures in accordance with embodiments of the invention, without undue experimentation.

Routes and Formulations

Compositions comprising EHP cells, including AMP cells, conditioned media derived therefrom, cell lysates derived therefrom, or cell products derived therefrom, each alone or in combination, or cells differentiated therefrom may be formulated in any conventional manner using one or more physiologically acceptable carriers optionally comprising excipients and auxiliaries. Proper formulation is dependent upon the route of administration chosen. The compositions of the invention may be packaged with written instructions for use of the cells in tissue regeneration, or restoring a therapeutically important metabolic function. The compositions may also be administered to the recipient in one or more physiologically acceptable carriers. Carriers for these cells may include but are not limited to solutions of phosphate buffered saline (PBS) or lactated Ringer's solution containing a mixture of salts in physiologic concentrations.

One of skill in the art may readily determine the appropriate concentration of EHP cells, including AMP cells, for a particular purpose. The skilled artisan will recognize that a preferred dose is one which produces a therapeutic effect, such as suppressing an inflammatory or immune response, in a patient in need thereof. Skilled artisans will also recognize that any and all of the standard methods and modalities for tissue, organ and cell-based transplantation therapies currently in clinical practice and clinical development are suitable for practicing the methods of the invention. Further, proper doses of EHP cells, including AMP cells, and cell lysates derived therefrom and conditioned media derived therefrom (i.e. ACCS), and dosing regimens are easily determined by those of skill in the art and need to be empirically determined at time of use based on several variables including but not limited to disease being treated; patient age, weight, sex, health; other medications and treatments being administered to the patient; and the like. Routes of administration, formulation, co-administration with other agents (if appropriate) and the like are discussed in detail elsewhere herein. A preferred dose is in the range of about $0.25$-$2.0 \times 10^6$ cells. Other preferred dose ranges are $0.1$-$10.0 \times 10^6$ cells per square centimeter of applied area based on in vitro as well as in vivo experiments. In a particular preferred embodiment, it has been found that relatively small amounts of EHP cells can suppress inflammatory and immune responses. For example, only 1,000-100,000 AMP cells per reaction in MLRs is sufficient to reduce T-cell response to potent stimulators by over 99% in vitro.

In addition, one of skill in the art may readily determine the appropriate concentration of conditioned media, including, for example, ACCS, for a particular purpose. A preferred dose is in the range of about 0.1-to-1000 micrograms per square centimeter of applied area. Other preferred dose ranges are 1.0-to-50.0 micrograms/applied area.

EHP cells, including AMP cells, conditioned media derived therefrom, cell lysates derived therefrom, or cell products derived therefrom, each alone or in combination, or cells differentiated therefrom can be administered by injection into a target site of a subject, preferably via a delivery device, such as a tube, e.g., catheter. In a preferred embodiment, the tube additionally contains a needle, e.g., a syringe, through which the cells can be introduced into the subject at a desired location. Specific, non-limiting examples of administering cells to subjects may also include administration by subcutaneous injection, intramuscular injection, or intravenous injection. If administration is intravenous, an injectable liquid suspension of cells can be prepared and administered by a continuous drip or as a bolus.

The compositions of the invention may also be inserted into a delivery device, e.g., a syringe, in different forms. For example, the cells can be suspended in a solution contained in such a delivery device. As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating EHP cells, including AMP cells, conditioned media derived therefrom, cell lysates derived therefrom, or cell products derived therefrom, each alone or in combination, or differentiated cells as described herein, in a pharmaceutically acceptable carrier or diluent and, as required, other ingredients enumerated above, followed by filter sterilization.

Undifferentiated, partially differentiated or fully differentiated EHP cells, including AMP cells, conditioned media derived therefrom, cell lysates derived therefrom, each alone or in combination, may be administered systemically (for example intravenously) or locally (for example directly into a myocardial defect under echocardiogram guidance or by direct application under visualization during surgery). For such injections, the compositions may be in an injectable liquid suspension preparation or in a biocompatible medium which is injectable in liquid form and becomes semi-solid at the site of damaged tissue. A conventional intra-cardiac syringe or a controllable endoscopic delivery device can be used so long as the needle lumen or bore is of sufficient diameter (e.g. 30 gauge or larger) that shear forces will not damage any cells being delivered.

Support matrices into which the EHP cells, including AMP cells, and/or cell lysates and/or conditioned media derived therefrom can be incorporated or embedded include matrices which are recipient-compatible and which degrade into products which are not harmful to the recipient. These matrices provide support and protection for undifferentiated and differentiated EHP cells in vivo and are, therefore, the preferred form in which such cells are transplanted into the recipient subjects.

Natural and/or synthetic biodegradable matrices are examples of such matrices. Natural biodegradable matrices include plasma clots, e.g., derived from a mammal, collagen, fibronectin, and laminin matrices. Suitable synthetic material for a cell transplantation matrix must be biocompatible to preclude migration and immunological complications, and should be able to support extensive cell growth and differentiated cell function. It must also be resorbable, allowing for a completely natural tissue replacement. The matrix should be configurable into a variety of shapes and should have sufficient strength to prevent collapse upon implantation. Recent studies indicate that the biodegradable polyester polymers made of polyglycolic acid fulfill all of these criteria (Vacanti, et al. J. Ped. Surg. 23:3-9 (1988); Cima, et al. Biotechnol. Bioeng. 38:145 (1991); Vacanti, et al. Plast. Reconstr. Surg. 88:753-9 (1991)). Other synthetic biodegradable support matrices include synthetic polymers such as polyanhydrides, polyorthoesters, and polylactic acid. Further examples of synthetic polymers and methods of incorporating or embedding cells into these matrices are also known in the art. See e.g., U.S. Pat. Nos. 4,298,002 and 5,308,701.

Attachment of the cells to the polymer may be enhanced by coating the polymers with compounds such as basement membrane components, agar, agarose, gelatin, gum arabic, collagens types I, II, III, IV and V, fibronectin, laminin, glycosaminoglycans, mixtures thereof, and other materials known to those skilled in the art of cell culture. All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

One of the advantages of a biodegradable polymeric matrix is that angiogenic and other bioactive compounds can be incorporated directly into the support matrix so that they are slowly released as the support matrix degrades in vivo. As the cell-polymer structure is vascularized and the structure degrades, EHP cells may differentiate according to their inherent characteristics. Factors, including nutrients, growth factors, inducers of differentiation or de-differentiation (i.e., causing differentiated cells to lose characteristics of differentiation and acquire characteristics such as proliferation and more general function), products of secretion, immunomodulators, inhibitors of inflammation, regression factors, biologically active compounds which enhance or allow ingrowth of the lymphatic network or nerve fibers, hyaluronic acid, and drugs, which are known to those skilled in the art and commercially available with instructions as to what constitutes an effective amount, from suppliers such as Collaborative Research, Sigma Chemical Co., vascular growth factors such as vascular endothelial growth factor (VEGF), epidermal growth factor (EGF), and heparin binding epidermal growth factor like growth factor (HB-EGF), could be incorporated into the matrix or be provided in conjunction with the matrix. Similarly, polymers containing peptides such as the attachment peptide RGD (Arg-Gly-Asp) can be synthesized for use in forming matrices (see e.g. U.S. Pat. Nos. 4,988,621, 4,792, 525, 5,965,997, 4,879,237 and 4,789,734).

In another example, the undifferentiated, partially differentiated or fully differentiated EHP cells, including AMP cells, may be transplanted in a gel matrix (such as Gelfoam from Upjohn Company) which polymerizes to form a substrate in which the cells can grow. A variety of encapsulation technologies have been developed (e.g. Lacy et al., Science 254:1782-84 (1991); Sullivan et al., Science 252:718-712 (1991); WO 91/10470; WO 91/10425; U.S. Pat. No. 5,837, 234; U.S. Pat. No. 5,011,472; U.S. Pat. No. 4,892,538). During open surgical procedures, involving direct physical access to the damaged tissue and/or organ, all of the described forms of undifferentiated, partially differentiated or fully differentiated EHP cell delivery preparations are available options. These cells can be repeatedly transplanted at intervals until a desired therapeutic effect is achieved.

The invention also provides for the delivery of EHP cells, including AMP cell compositions described herein, in conjunction with any of the above support matrices as well as amnion-derived membranes. Such membranes may be obtained as a by-product of the process described herein for the recovery of AMP cells, or by other methods, such as are described, for example, in U.S. Pat. No. 6,326,019 which describes a method for making, storing and using a surgical graft from human amniotic membrane, US 2003/0235580 which describes reconstituted and recombinant amniotic membranes for sustained delivery of therapeutic molecules, proteins or metabolites, to a site in a host, U.S. 2004/0181240, which describes an amniotic membrane covering for a tissue surface which may prevent adhesions, exclude bacteria or inhibit bacterial activity, or to promote healing or growth of tissue, and U.S. Pat. No. 4,361,552, which pertains to the preparation of cross-linked amnion membranes and their use in methods for treating burns and wounds. In accordance with the present invention, EHP cells may be grown on such membranes, added to the membrane in either an undifferentiated, partially differentiated or fully differentiated form, or conditioned media or cell lysates may be added to such membranes. Alternatively, amniotic tissue in which AMP cells have not been stripped away may be used to deliver EHP cells to a particular site. In all cases, EHP cells used in conjunction with amniotic tissue or other matrices can be used in combination with other therapeutically useful cells and/or cells expressing biologically active therapeutics such as those described in below.

EHP cells may be genetically engineered to produce a particular therapeutic protein. Therapeutic protein includes a wide range of biologically active proteins including, but not limited to, growth factors, enzymes, hormones, cytokines, inhibitors of cytokines, blood clotting factors, peptide growth and differentiation factors. Particular differentiated cells may be engineered with a protein that is normally expressed by the particular cell type. For example, pancreatic cells can be engineered to produce digestive enzymes. Hepatocytes can be engineered to produce the enzyme inhibitor, A1AT, or clotting factors to treat hemophilia. Furthermore, neural cells can be engineered to produce chemical transmitters.

Methods which are well known to those skilled in the art can be used to construct expression vectors containing a nucleic acid encoding the protein of interest linked to appropriate transcriptional/translational control signals. See, for example, the techniques described in Sambrook et al, 2001, "Molecular Cloning: A Laboratory Manual"; Ausubel, ed., 1994, "Current Protocols in Molecular Biology" Volumes I-III; Celis, ed., 1994.

Suitable methods for transferring vector or plasmids into EHP cells or cells differentiated therefrom include lipid/DNA complexes, such as those described in U.S. Pat. Nos. 5,578,475; 5,627,175; 5,705,308; 5,744,335; 5,976,567; 6,020,202; and 6,051,429. Suitable reagents include lipofectamine, a 3:1 (w/w) liposome formulation of the poly-cationic lipid 2,3-dioleyloxy-N-[2(sperminecarbox-amido)ethyl]-N,N-d-imethyl-1-propanaminium trifluoroacetate (DOSPA) (Chemical Abstracts Registry name: N-[2-(2,5-bis[(3-aminopropyl)amino]-1-oxpentyl)amino)ethyl-]-N,N-dimethyl-2,3-bis(9-octadecenyloxy)-1-propanamin-trifluoroacetate), and the neutral lipid dioleoyl phosphatidylethanolamine (DOPE) in membrane filtered water. Exemplary is the formulation Lipofectamine 2000™ (available from Gibco/Life Technologies #11668019). Other reagents include: FuGENE™ 6 Transfection Reagent (a blend of lipids in non-liposomal form and other compounds in 80% ethanol, obtainable from Roche Diagnostics Corp. #1814443); and LipoTAXI™ transfection reagent (a lipid formulation from Invitrogen Corp., #204110). Transfection of EHP cells can be performed by electroporation, e.g., as described in Roach and McNeish (Methods in Mol. Biol. 185:1 (2002)). Suitable viral vector systems for producing stem cells with stable genetic alterations may be based on adenoviruses, lentiviruses, retroviruses and other viruses, and may be prepared using commercially available virus components.

The invention is further illustrated by the following examples, which should not be construed as further limiting as the scope of the invention can only be determined by the claims.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Characterization of Amnion-Derived Multipotent Progenitor (AMP) Cells Used in Studies For immunological studies, a further characterization of the cell surface markers of AMP cells, a distinct sub-population of cells isolated from human amnion that have been cryopreserved, cultured, and propagated, was performed before examination of their immunological characteristics. Under these conditions, AMP cells are negative for the CD117 antigen (c-kit), distinguishing AMP cells from amniotic fluid-derived cells, and are ~74% positive for CD90 and ~97% SSEA-4. AMP cells also exhibit staining for CD9 (~81%), CD10 (~64%), CD29 (~100%), CD104 (~100%), CD49f (~100%), CD105 (~12%) and CD44 (~7%), but are negative for hematopoietic markers CD34 and CD45 and for the PDGF receptor CD140b. Further analysis was performed to establish a relevant immunological profile for AMP cells. AMP cells expressed MHC class I molecules, however were negative for MHC Class II. AMP cells were also negative for the co-stimulatory molecules CD80 and CD86 (B7-1 and B7-2, respectively). The expression of these markers was unaffected by incubation in the presence of IFN-γ. AMP cells were shown to have Fas expression, possibly providing a mechanism against FasL-expressing activated effector cells in vivo. Consistent with other findings of placenta-derived cells, AMP cells we found to be positive for both PD-L1 and PD-L2 after exposure to IFN-γ. Finally, AMP cells express the non-classical HLA class I antigen HLA-G, a key component of the immuno-modulatory effects of the amnion itself. HLA-G was present on ~60-90% of cells at the time of isolation, and decreased gradually over passage. HLA-G expression was up-regulated by the addition of IFN-γ. AMP cells were negative, however, for the non-classical HLA class I receptors IL-T2, IL-T3, and IL-T4 at all times tested. These molecules are up-regulated by HLA-G itself, but the lack of these receptors on AMP cells may indicate the absence of any autocrine regulation by HLA-G on the cell surface.

Example 2

Immunogenicity of AMP Cells: Mixed Lymphocyte Reaction (MLR). Normal Peripheral Blood Mononuclear Cells vs. HLA-DR (Class II) Mismatched AMP Cells HLA-G is a non-classical major histocompatibility complex (MHC) class I molecule that has a tissue-restricted distribution. It has been shown to provide materno-fetal tolerance and is expressed on cytotrophoblasts at the fetal-maternal interface. HLA-G is also expressed by certain cancer lineages, where it may have a role in providing an escape mechanism to the immuno-surveillance of the host organism. It has been shown (CMLS, 55, 1999, 327-333, incorporated by reference herein) that HLA-G can inhibit MHC-restricted (T-cell) and unrestricted (NK cell) responses through Killing Inhibitory Receptors (KIR) expressed on the T-cell and NK cells. This includes lytic as well as proliferative responses. Therefore, HLA-G has immunomodulatory properties of the cells expressing it and of the environment in which these cells are located.

Applicants have found that AMP cells variably express the HLA-G cell surface marker upon isolation from the amnion (>60%, n=20); however, the expression of this marker decreases as the cells are cultured over time. When pro-inflammatory cytokines (IFNγ (100 IU/mL) alone or with TNFα (10 ng/mL) and IL1β (10 ng/mL)) are added to the culture, HLA-G expression is up-regulated. In addition, the MHC Class II markers (i.e. DR, DP, DQ) are not expressed by AMP cells either at isolation or after culture with or without pro-inflammatory cytokines. Applicants have also have found that AMP cells do not express the co-stimulatory molecules CD80 and CD86, which are pivotal in signaling a normal immune response. Since AMP cells have no MHC Class II or co-stimulatory molecule expression and have HLA-G expression on the cell surface, it is theorized that AMP cells will not illicit a T helper immune response and may have immunomodulatory properties.

To test this hypothesis and determine the immunogenic potential of AMP cells, both at isolation and after culture, the cells were tested in a standard mixed lymphocyte reaction (MLR) (see, for example, Bach, F. H., Hirschorn, H. "Lymphocyte interaction: A potential histocompatibility test in vitro. Science 1964; 143:813-814. Bain, B., Vaz, M R, Lowenstein, L. "The development of large immature mononuclear cells in mixed lymphocyte cultures." Blood 1964; 23:108-116. Jeras, M. "The role of in vitro alloreactive T-cell functional tests in the selection of HLA matched and mismatched haematopoietic stem cell donors." Transplant Immunology 2002; 10:205-214, all of which are incorporated herein by reference).

Responder cell populations consisted of ficoll-hypaque-isolated peripheral blood mononuclear cells. Two normal volunteers (Responder 1 and Responder 2) with mismatched HLA-DR loci were chosen. Stimulator cell populations consisted of AMP cells that were tissue-typed at the DNA level and found to mismatch both normal responders. Normal responders were also used as stimulators against each other as a positive control. Stimulator cell populations were irradiated with 2000 Rads to prevent proliferation during the one-way MLR. Cells were mixed at 100,000 cells responders vs. 100,000 cells stimulators in one well of a 96-well plate and run in triplicate. Cultures were incubated for 6 days and were then pulsed with tritiated Thymidine for 1 day and then harvested and counted using a beta-scintillation counter. The results of this experiment are shown in FIG. 1.

Figure 1:
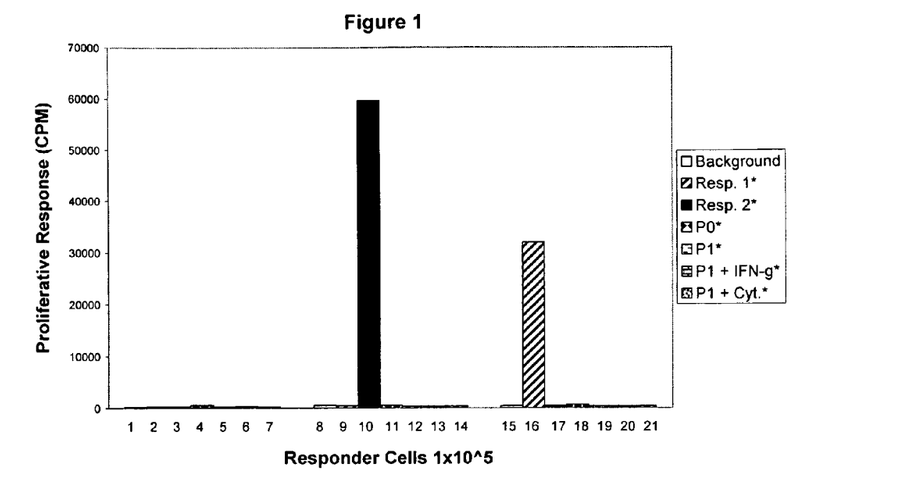
FIG. 1: Mixed lymphocyte reaction (MLR). Normal peripheral blood mononuclear cells vs. HLA-DR (Class II) mismatched AMP cells.

Responder cells are listed as numbers 1-21 on the X axis of FIG. 1. Numbers 1-7 represent AMP cells vs. irradiated (asterisk) stimulator cells shown in the legend. Numbers 8-14 represent Responder 1 vs. irradiated stimulator cells shown in the legend. Numbers 15-21 represent Responder 2 vs. irradiated stimulator cells shown in the legend.

Normal PBMCs did not respond to any of the irradiated stimulator AMP cells shown in FIG. 1. Normal HLA-DR mismatched responders (1 and 2) only had a positive reaction by MLR when cultured with each other. There was no significant response of either normal responder vs. irradiated AMP cells at either the non-passaged time point (P0), or when cultured longer after one passage (P1). Pro-inflammatory cytokine addition (IFN-γ alone or IFN-γ, IL-1, and TNF-α) did not augment a response of either normal responders to AMP cells, but these cytokines may have been toxic at the same time. These data suggest that AMP cells are not capable of generating an immune response at the helper T-cell level.

Example 3

Immunomodulatory Effects of AMP Cells: Mitogen Response, Mixed Lymphocyte Reaction, and Antigen-Specific Memory Response to Cytomegalovirus (CMV)

Figure 2:
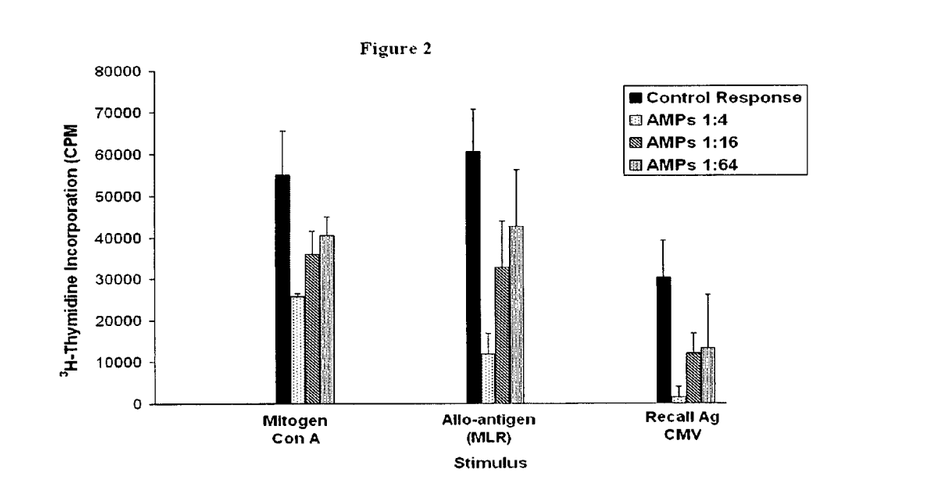
FIG. 2: Normal mononuclear cell response to mitogen, MLR, and recall antigen cytomegalovirus (CMV) plus the addition of HLA-DR (Class II) mismatched AMP cells.

Normal PBMCs respond vigorously to stimulation with the mitogen Concanavelin A (Con A) in a three day culture. To assess the immunomodulatory effects of AMP cells on Con A stimulation, various concentrations of AMP cells were titrated into the assay. Briefly, PBMCs were cultured at $1\times10^5$ cells per well in a 96-well round bottom tissue culture plate (BD Falcon, Cat. #08-772-5) in the presence of 10 µM Con A (Sigma, Cat. #C5275). The cultures were incubated at 37° C. in a humidified 5% $CO_2$ incubator for 2 days, then pulsed overnight with 1 µCi tritiated thymidine ($^3$H-dTR, Perkin Elmer, Waltham, Mass.) to measure T cell proliferation. Cultures were then harvested using a Mach III 96-well cell harvester (Tomtec, Hamden, Conn.) and counted using a Microbeta scintillation counter (Wallac Inc., Gaithersburg, Md.). The results were expressed as mean values of triplicate cultures in counts per minute (CPM) and are shown in FIG. 2. AMP cells were co-cultured with the PBMCs and mitogen at 1:4, 1:16 and 1:64 dilutions. Positive controls consisted of PBMC plus mitogen alone. Negative controls consisted of PBMC alone and AMP cells alone in culture media. All cultures were harvested and counted at day 3. Inhibition of T cell proliferation was determined by the percent reduction in CPM from wells containing AMP cells vs. the total proliferation of PBMC to Con A.

The one-way MLR was used to assess T cell reactivity vs. allogeneic stimulation. To identify whether AMP cells were immunogenic to allogeneic PBMCs, responder PBMCs were cultured in 200 µl RPMI+5% human AB serum at a concentration of $1\times10^5$ cells per well in a 96-well round bottom tissue culture plate along with stimulator 2000 rad-irradiated AMP cells at the same concentration in triplicate. The cultures were incubated at 37° C. in a humidified 5% $CO_2$ incubator for 6 days, then pulsed for 6 hours with 1 µCi tritiated thymidine to measure T cell proliferation. The results were expressed as mean values of triplicate cultures in counts per minute (CPM) and are shown in FIG. 2. This experiment was repeated several times using two normal PBMC populations with mismatched HLA DR alleles. The positive control included MLR cultures between two HLA-DR mismatched PBMCs. Negative controls consisted of responder and stimulator cells alone in RPMI+5% AB serum and responder cells vs. themselves (irradiated). To assess the immunomodulatory characteristics of AMP cells in vitro, AMP cells were serially titrated into a MLR between PBMCs isolated from normal volunteers with mismatched HLA-DR alleles. Stimulator PBMCs and AMP cells were irradiated with 2000 rads to prevent proliferation. AMP cells were titrated into the MLR at a starting concentration 1:4, and further diluted to 1:16, and 1:64. T cell proliferation was measured as described above. Inhibition of T cell proliferation was determined by the percent reduction in CPM of wells containing AMP cells vs. the total proliferation between normal responders and stimulators.

The immunomodulatory effects of AMP cells on the recall memory response of T cells to Cytomegalovirus (CMV) antigen was also tested. Normal CMV seropositive PBMCs were isolated as described above and cultured in the presence of soluble CMV antigen at $1\times10^5$ cells per well in 96-well plates in triplicate. 2000 rad-irradiated AMP cells were titrated into the cell culture wells at a starting concentration of 1:4, and further diluted to 1:16 and 1:64. These cultures were incubated at 37° C. in a humidified 5% $CO_2$ incubator for 6 days, then pulsed for 6 hours with 1 µCi tritiated thymidine to measure T cell proliferation. The results are expressed as mean values of triplicate cultures in counts per minute and are shown in FIG. 2. The positive control consisted of PBMCs in the presence of CMV antigen alone. Negative controls consisted of responder PBMCs and AMP cells alone in culture media. Inhibition of T cell proliferation was determined by the percent reduction in CPM of wells containing AMP cells vs. the total proliferation of PBMC to soluble CMV antigen.

Results: In the absence of AMP cells, T cells responded vigorously to stimulation with Con A, allogeneic MLR, and to CMV antigen. Significant inhibition occurred when AMP cells were titrated into these assays in a dose-dependent manner ($p<0.01$). This dose effect was most prevalent for in the recall antigen assay, where seropositive T cells were inhibited by an average of 95% by AMP cells titrated into the assay at a dilution of 1:4. Results were reproducible when seven CMV seropositive responders were tested against soluble CMV antigen in the presence of four different AMP populations. This effect was also observed in the allo-antigen MLR, where average inhibition reached 80.1% inhibition. Again, seven different sets of responders and mismatched stimulators were used with four different AMP populations in these assays. In contrast, Con A response reached only 51.6% inhibition in the presence of AMP cells at this dilution. Six different responders were tested against soluble mitogen with four different AMP cell populations. These inhibitory effects of AMP cells were unaffected by the addition or pre-incubation of AMP cells with IFN-γ. IFN-γ also did not up-regulate MHC class II expression on AMP cells at any time, but HLA-G expression was up-regulated to over 60% on AMP cells surface (FIG. 2). As AMP cells were further diluted to 1:16, there was still significant dose-dependent inhibition in all three assays tested, but this effect was not equally distributed. The highest inhibition was observed with CMV-specific responses at an average of 62%, whereas the allo-antigen and the mitogen responses dropped to an average of 47% and 34% inhibition, respectively. At the final dilution of AMP cells used in these assays (1:64), only the recall response to CMV remained inhibited by more than 50%.

Example 4

Effects of Passaging and Dose Response of AMP Cells on Allo-Antigen MLR

Figure 3:
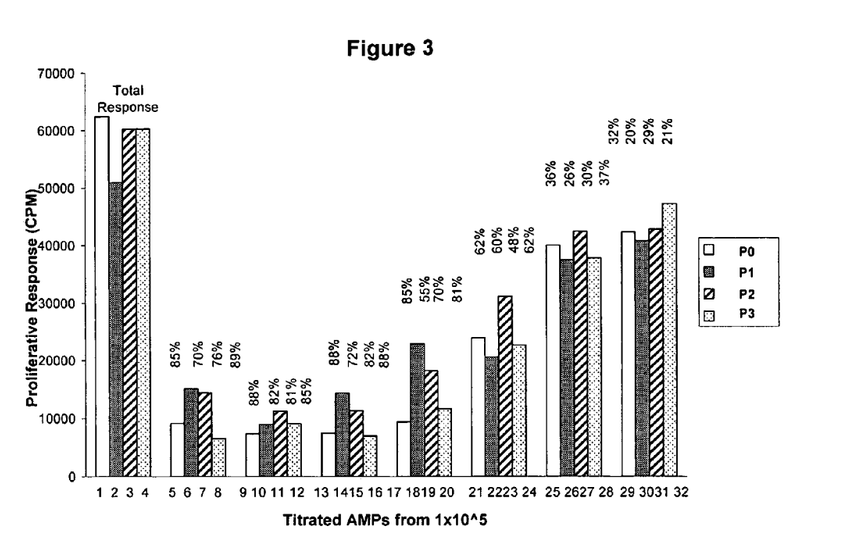
FIG. 3: Effects of serially diluted AMP cells on Allo-Antigen MLR.

AMP cells were isolated from various time points in culture and passaged. P0 is the earliest time point and are non-passaged cells. P1, P2, and P3 refer to passage numbers with P1 being cells taken after the first passage, P2 the second, and P3 the third. After collection, the AMP cells were irradiated and placed into a normal MLR between responders 1 and 2 at $1\times10^5$ starting concentration. AMP cells were then serially diluted from this starting concentration down to 1:64 and added to the MLR to see the effects of lower cell numbers on inhibition. FIG. 3 shows the results of this experiment.

The total uninhibited response between normal responders 1 and 2 by MLR are shown as numbers 1-4 on the X axis of FIG. 3. Inhibitory effects of P0, P1, P2, and P3 AMP cell titrations are represented by numbers 5-32 on the X axis.

The results show significant inhibition of the normal MLR with no impact of passage time of the AMP cells. MLR was inhibited by up to 89% at the highest AMP cell dilution. A titration effect was observed, with AMP cell inhibition remaining over 20% even at the 1:64 dilution. In these AMP cells, HLA-G expression was measured at ~52% at isolation or P0 and was still detected at P3 being (~12%).

Example 5

Effects of Passaging and Dose Response of AMP Cells on Memory Response to Cytomegalovirus (CMV)

The immunomodulatory characteristics of AMP cells was also assessed by a second experiment in which the AMP cells were irradiated and serially diluted as before, but instead of culturing in a normal MLR, the cells were titrated into a recall antigen memory response to Cytomegalovirus assay. Responder 2 is also a CMV sero-positive responder. When cultured with isolated CMV antigen, there is a high response as measured by a stimulation index of $H^3$ Thymidine incorporation. This is a classical memory response to an antigen that these cell lineages were previously exposed to. When AMP cells were titrated into this system, there was an abrogation of this memory response, as shown by FIG. 4.

Figure 4:
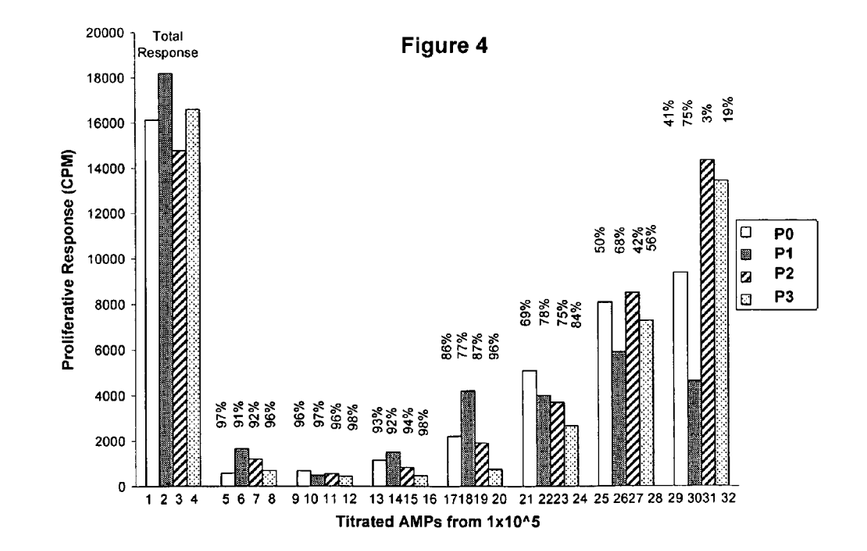
FIG. 4: Effects of serially diluted AMP cells on memory response to cytomegalovirus (CMV).

The total uninhibited response between the sero-positive responder and CMV antigen is represented as numbers 1-4 on the X axis of FIG. 4. The effect of titrated AMP cells at P0, P1, P2, and P3 is represented by numbers 5-32 on the X axis of FIG. 4.

The normal CMV response was inhibited by greater than 90% using the first 3 serial dilutions of the AMP cells titrated into the culture (1:1, 1:2, and 1:4). This inhibition steadily dropped with further titrations. There was no significant effect of passage number on the inhibition results shown. Taken together, these data illustrate that AMP cells appear to have an immunomodulatory function and can down-regulate the immune response.

Example 6

Immunomodulatory Effect of the AMP Cells is not a Cytotoxic Effect

To confirm that the effect seen in is an immunomodulatory effect of the AMP cells and not a cytotoxic effect, co-culture experiments were performed to assess responder growth and viability. The results of this experiment demonstrate that PBMC responders co-cultured with AMP cells have slightly lower viability than PBMC responders alone. PBMC responders to allogeneic PBMC cultured with AMP cells had a slight decrease in viability as well. However, PBMC responders to allogeneic PBMC responders without AMP cells also showed some decrease in viability. This decrease in viability may have been due to inappropriate length of experimental culture.

Example 7

Effect of AMP Cells on Growth Factor-Induced Cell Culture: IL-2 T Cell Blasts and Epstein-Barr Virus (EBV)-Transformed B Cells AMP cells were analyzed for potential immunomodulation of pre-activated T and B cell cultures. IL-2-dependent T cell blasts were produced by culturing $10\times10^6$ PBMC in the presence of 10 μM Phytohaemagglutinin (PHA, Sigma Cat. #L2646) and 10U rhIL-2 (Peprotech, Cat. #200-02) over a period of 5 days in 20 mls RPMI+5% human AB serum in 25 cm² tissue culture flasks (BD Falcon, Cat. #08-772-18). IL-2-dependent cells were then collected by centrifugation and washed once and transferred to 96-well tissue culture-treated plates at a concentration of $1\times10^5$ cells per well in fresh RPMI+5% human AB serum. Cells were then re-exposed to IL-2 for three days and measured for proliferation by uptake of $^3$H-dTR as described above. AMP cells were added to these cells at this time at a titration dilution of 1:5, 1:10, 1:50, 1:100, 1:500, and 1:1000 to assess immunomodulatory effects. The positive control consisted of T cell blasts in culture media in the presence of IL-2. Negative controls consisted of T cell blasts in culture media without IL-2 and AMP cells alone in culture media. Inhibition of blast proliferation in response to IL-2 was determined by the percent reduction in CPM of wells containing AMP cells vs. the total proliferation of T cell blasts to IL-2.

Transformed B cell blasts were created by culturing PBMC in the presence of Epstein-Barr virus as previously described (Pope, J., Scott, W., Moss, D., Human lymphoid cell transformation by Epstein-Barr virus. National Review of Biology, 1973. 246: p. 140-141). These pre-activated blasts exhibit self-sustained proliferation when grown in media containing fetal calf serum. Blasts were cultured at $1 \times 10^5$ cell per well in RPMI+10% fetal calf serum. AMP cells were added to these cells at the same dilutions as above to assess effects on B cell blast proliferation. The positive control was B cell blasts in media alone. Negative controls consisted of B cell blasts alone in media without fetal calf serum and AMP cells alone in culture media. Inhibition of blast proliferation was determined by the percent reduction in CPM of wells containing AMPs vs. the total proliferation of B cell blasts in media with fetal calf serum.

Results: The IL-2 T cell blasts proliferated in response to exogenous IL-2 with a range of 3560-12811 CPM. There was no inhibition of proliferation of the T cell blasts to re-exposure to IL-2 using any dilution of AMP cells tested. Indeed, the range of proliferative inhibition was 3472-12041 CPM, respectively (n=3). These results were consistently repeated with any dilution of AMP cells used, although the variability was high due to large differences in T cell blast proliferation. Similar results were found when AMP cells were co-cultured with B cell blasts in the presence of fetal calf serum in the culture media (n=6). One example showed B cell proliferation in culture media alone at 1259 CPM. Upon the addition of AMP cells at a 1:4 ratio (the highest amount), there was no inhibitory effect with CPM remaining at 1701. At no dilution did AMP cells inhibit B cell blast proliferation to growth factors in culture media. Therefore, there was a total lack of dose-dependent inhibition by AMP cells seen on growth factor-activated cells.

Example 8

Transwell Assays and Conditioned Media

Non-irradiated AMP cells were plated into the upper chamber of 24-well transwell plates (Corning, 4 µm pore size, Cat. #3413) at a confluent density of $5 \times 10^5$ AMP cells per well. Mitogen stimulation assays were set up in the lower chambers consisting of $5 \times 10^5$ PBMC isolated from normal donors and 10 µg/ml Concanavelin A. After 3 days in culture, cells from the lower chamber were transferred to 96-well round bottom plates in triplicate (200 µl/well) and pulsed with $^3$H-dTR and harvested 18 hours later. Comparison groups consisted of normal PBMC plus mitogen alone, with AMP cells titrated into the wells at 1:5, 1:50, and 1:500 dilution, versus AMP cells at the same titrations separated from the PBMC and mitogen by the transwell membrane apparatus. Data are represented as percentage of proliferation (proliferation index), where T cells in the presence of mitogen stimulation alone equaled 100%. Inhibition in proliferation index was calculated by subtracting the percent inhibition of cultures in the presence of AMP cells plus stimulation from cultures with stimulation alone.

Conditioned media was removed from AMP cell cultures after growth reached near-confluency in T-75 tissue culture flasks (Fisher Scientific, Cat. #13-680-58). Conditioned media was immediately added to mitogen, MLR, and recall antigen assays described above by serial dilution yielding final dilutions of 1:2, 1:4, and 1:8 within each experiment. Positive controls included PBMC plus mitogen alone, PBMC plus irradiated allo-PBMC alone, and PBMC plus CMV antigen alone. Negative controls were PBMC in culture media alone and PBMC in conditioned media alone at each dilution with culture media. Data are represented as percentage of proliferation (proliferation index), where T cells in the presence of mitogen stimulation alone equaled 100%. Inhibition in proliferation index was calculated by subtracting the percent inhibition of cultures in the presence of AMPs plus stimulation from cultures with stimulation alone.

Results: In the transwell system, AMP cells were unable to suppress PBMCs from proliferating in response to mitogen. Normal PBMC response to mitogen alone represents a proliferation index of 100% (control). As shown above, AMP cells inhibit this response in a dose-dependent manner. Here, AMP cells were titrated into the assay at dilutions of 1:5, 1:50, and 1:500. AMP cells reduced the stimulation index from 100% down to an average of 50±8.9% at 1:5, 56.7±7.4% at 1:50, and 72±10.8% at 1:500. When AMP cells were separated from PBMC and mitogen via transwells, there was no inhibition in the stimulation index. Indeed, at the dilution of 1:5 AMP cells, the proliferation index actually increased by 19.1±14.6 above the control. At 1:50, there was a drop in proliferation to 90.1±12.1% and at 1:500 there was a slight increase by 2.3±29.5%. The reason standard deviations were considerably higher with the transwells may be because of the assay conditions employed, resulting in unequal amounts of responding T cells being transferred between the plates, thus contributing to the wide range of CPMs recorded. Regardless, AMP cells were still unable to significantly inhibit T cell responses to mitogen. Indeed, counts were actually slightly higher in two of the three dilutions examined (1:5 and 1:500).

The immunomodulatory effect of conditioned media taken from AMP cells in culture on mitogen, allo-antigen (MLR) and recall antigen to CMV assays was also examined. Conditioned media at the highest concentration (1:2 dilution) slightly diminished PBMC response to mitogen and had a greater inhibition to MLR and recall antigen responses, but did not reach statistical significance due to high variability. There was no inhibition at all at the 1:4 and 1:8 dilutions tested. Taken together, these data suggest that AMP cells require cell-to-cell contact to elicit an immunomodulatory effect and that this effect is not mediated by soluble factors.

Throughout the specification various publications have been referred to. It is intended that each publication be incorporated by reference in its entirety into this specification.

We claim:

1. A method for down-regulating the immune response a subject's peripheral blood mononuclear cells (PBMCs) exhibit when they are exposed to an antigen present on a transplanted tissue, the method comprising the step of contacting the subject PBMCs with a purified population of CD117-negative Amnion-derived Multipotent Progenitor (AMP) cells prior to exposure of the subject to the transplanted tissue, such that the AMP cells down-regulate the immune response exhibited by the PBMCs upon exposure to the transplanted tissue.

2. The method of claim 1 wherein the immune response is an autoimmune response.

3. The method of claim 1 wherein the immune response is an allogeneic response.

4. The method of claim 1 wherein the PBMCs are further contacted with one or more active agents.

5. The method of claim 4 wherein the one or more active agents is selected from the group consisting of a corticosteroid, a cyclosporine, a tacrolimus, a sirolimus, a methotrexate, an azathiopine, a mercatopurine, a cytotoxic antibiotic, a polyclonal antibody, a monoclonal antibody, an interferon, an opioid, a TNF binding protein, a mycophenolate, a FTY720, and another cell type.

6. The method of claim 5 wherein the monoclonal antibody is selected from the group consisting of an anti-T-cell receptor (CD23) and an anti-IL2 receptor (CD25) antibody.

* * * * *